United States Patent [19]

Palmer et al.

[11] Patent Number: 5,330,424

[45] Date of Patent: Jul. 19, 1994

[54] MEDICAL LAVAGE APPARATUS AND METHODS

[75] Inventors: Darrel Palmer, Sandy; William R. Houghton, Midvale, both of Utah

[73] Assignee: Ballard Medical Products, Draper, Utah

[21] Appl. No.: 82,179

[22] Filed: Jun. 24, 1993

Related U.S. Application Data

[62] Division of Ser. No. 923,706, Jul. 31, 1992, Pat. No. 5,254,086.

[51] Int. Cl.⁵ .............................................. A61M 5/00
[52] U.S. Cl. ...................................... 604/28; 604/49; 604/181
[58] Field of Search ............. 604/28, 38, 49, 181, 604/187, 191, 247, 256

[56] References Cited

U.S. PATENT DOCUMENTS

| | | |
|---|---|---|
| 13,975 | 12/1855 | Buhler . |
| 386,603 | 7/1888 | Parsons . |
| 1,496,126 | 6/1924 | Livingstone . |
| 3,159,312 | 12/1954 | VanSciver II ............... 222/137 |
| 3,398,743 | 8/1968 | Shalit ........................... 128/214 |
| 3,450,134 | 6/1969 | Willgerodt ................... 128/214 |
| 3,818,907 | 6/1974 | Walton ......................... 604/38 |
| 3,828,980 | 8/1974 | Creighton ..................... 222/386 |
| 4,044,757 | 8/1977 | McWhorter ................... 604/220 |
| 4,046,166 | 9/1977 | Bender ...................... 137/625.48 |
| 4,054,137 | 10/1977 | Lee et al. ..................... 604/38 |
| 4,260,077 | 4/1981 | Schroeder ..................... 604/191 |
| 4,535,818 | 8/1985 | Duncan et al. ................ 806/247 |
| 4,643,723 | 2/1987 | Smit ............................. 604/207 |
| 4,662,868 | 5/1987 | Cambio ......................... 604/38 |
| 4,683,916 | 8/1987 | Raines .......................... 604/247 |
| 4,842,581 | 6/1989 | Davis ............................ 604/38 |
| 4,857,056 | 8/1989 | Talonn .......................... 604/191 |
| 4,872,866 | 10/1989 | Davis ............................ 604/227 |
| 4,883,456 | 11/1989 | Holter ........................... 604/247 |
| 4,883,471 | 11/1989 | Braginetz et al. ............. 604/218 |
| 4,921,488 | 5/1990 | Maitz et al. ................... 604/247 |
| 4,979,942 | 12/1990 | Wolf et al. .................... 604/191 |
| 5,049,135 | 9/1991 | Davis ............................ 604/181 |
| 5,098,405 | 3/1992 | Peterson et al. .............. 604/247 |
| 5,156,600 | 10/1992 | Young .......................... 604/247 |
| 5,169,393 | 12/1992 | Moorehead et al. .......... 604/247 |

FOREIGN PATENT DOCUMENTS 279033 2/1970 Austria .

*Primary Examiner*—Paul J. Hirsch
*Attorney, Agent, or Firm*—Lynn G. Foster

[57] ABSTRACT

A medical lavage apparatus for body cavities comprising a housing having parallel irrigation and aspiration cylinders with captive plungers extending in bores thereof from a first end and pairs of check-valves positioned in parallel, smaller, offset cylinders located at second ends such that reciprocal movement of the each plunger in each cylinder performs the function of a one-way pump. The plungers are held captive and aligned by guide-stops proximally disposed in each cylinder. Each plunger comprises a seal disposed at the distal end thereof which inhibits communication between the pairs of check-valves in each cylinder when the plunger is fully seated in the cylinder. Novel jam-free dome shaped, slit check-valves are disposed to be the pair of check-valves in the aspiration cylinder in one embodiment and in irrigation cylinders as well in other embodiments. The dome shaped valves are described for use in other medical fluid control applications, as well. A septum formed of intersecting semi-circular-in-cross-section baffles joins the adjacent outer ends of the irrigation and aspiration check-valve cylinders so as to allow full fluid streams flowing from these outer ends to flow together at an angle. The septum and associated irrigation and aspiration check-valve cylinders are enclosed in a common exchange tube which leads to a common patient tube connecting nozzle. A special patient tube securing attachment is disposed on the connecting nozzle.

5 Claims, 3 Drawing Sheets

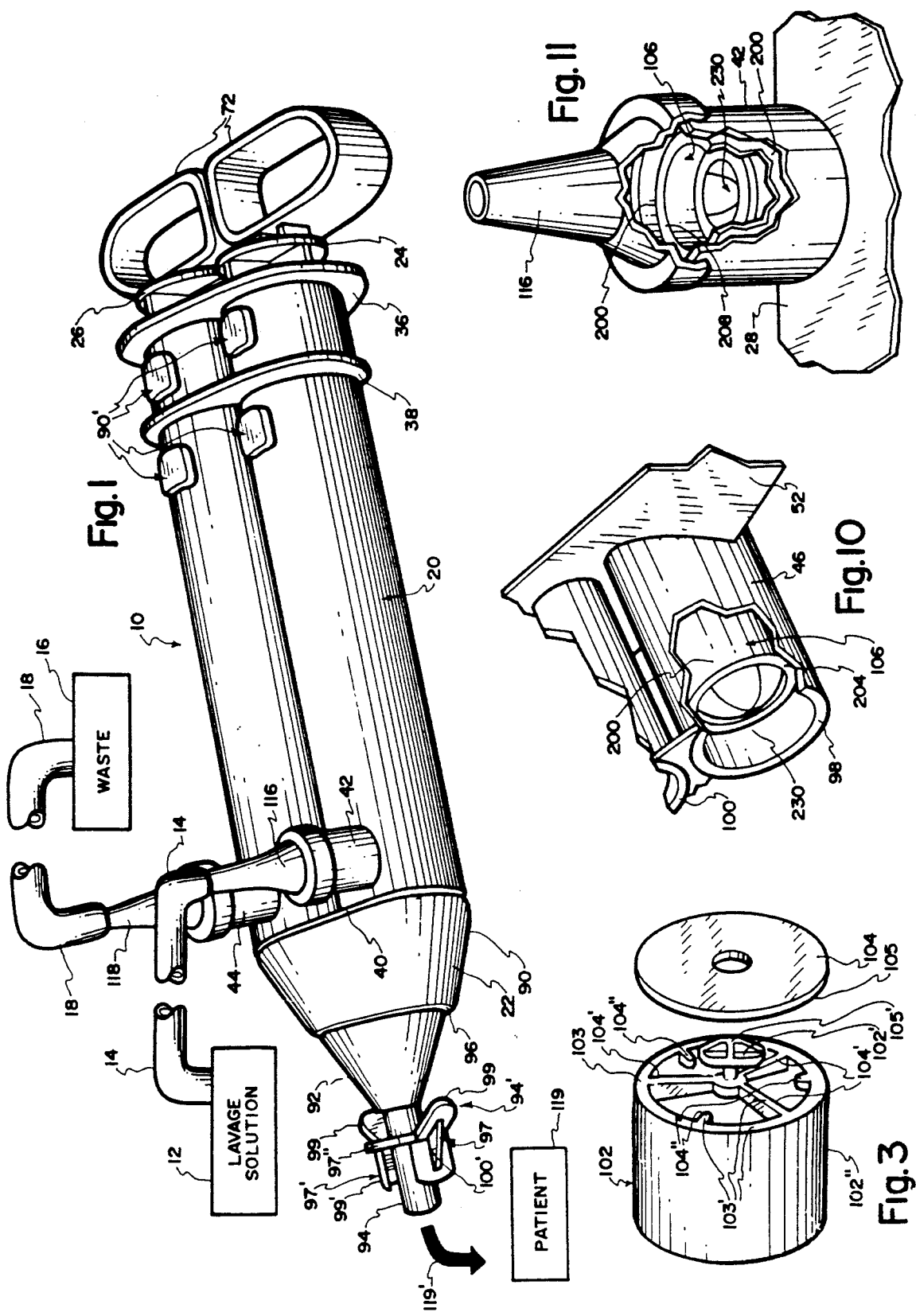

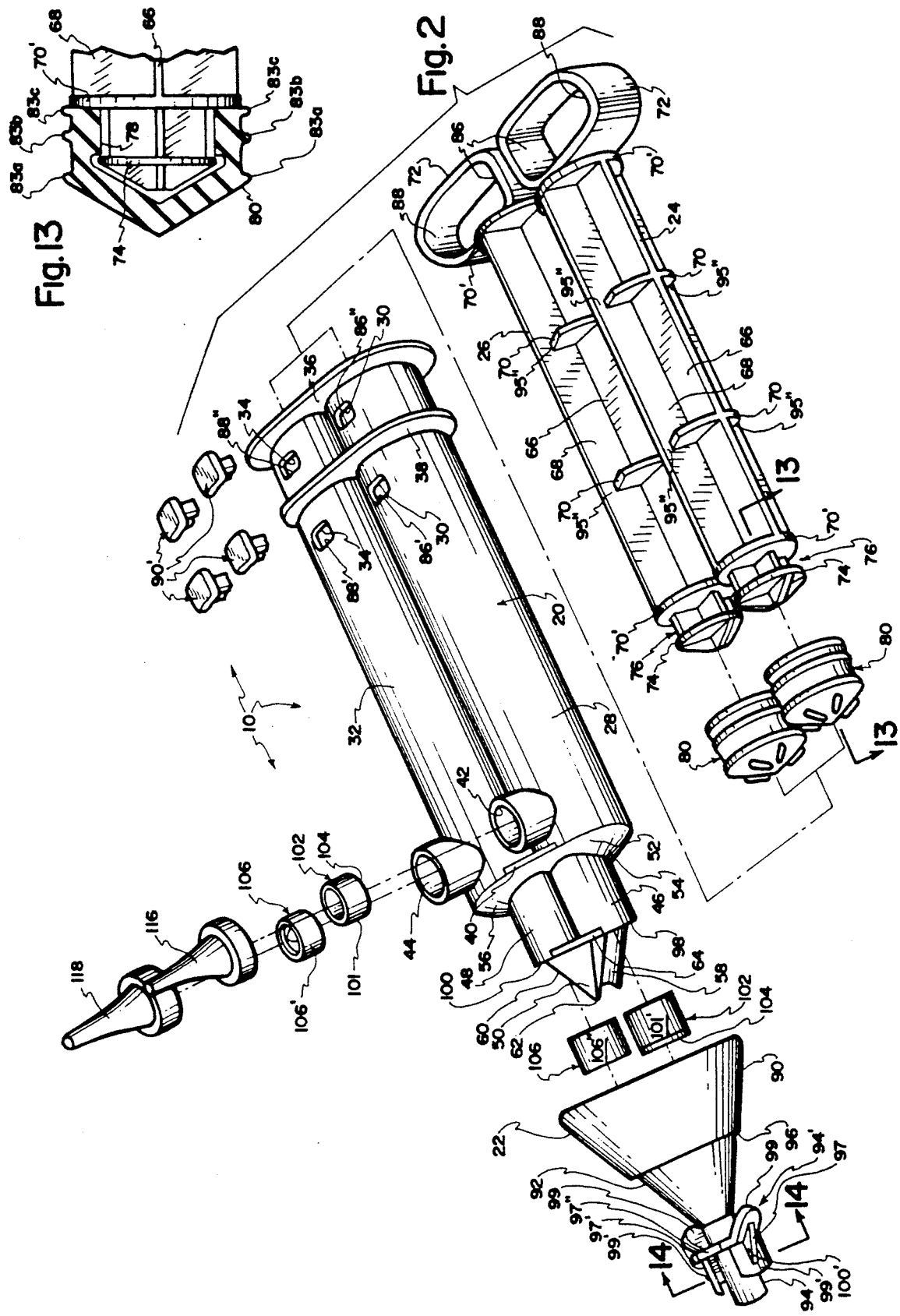

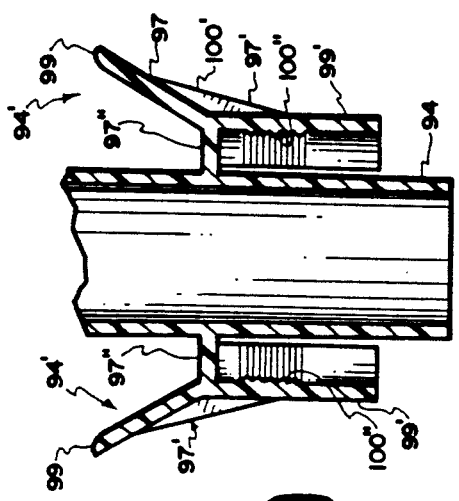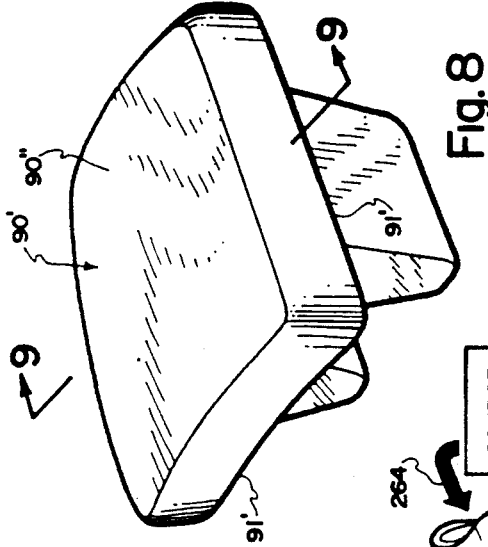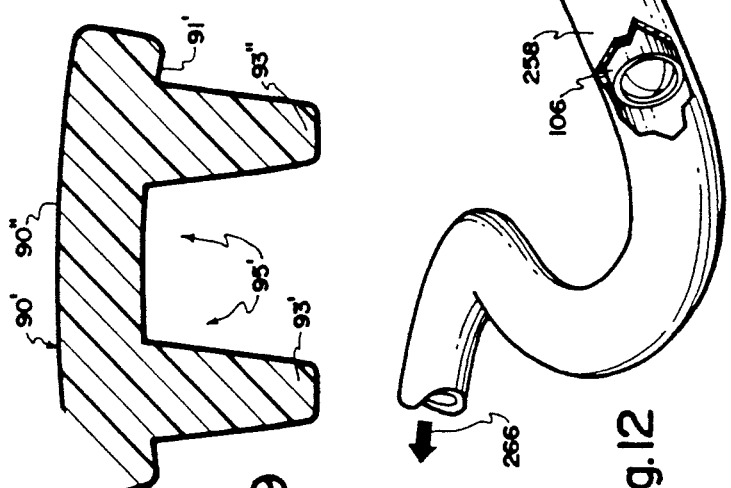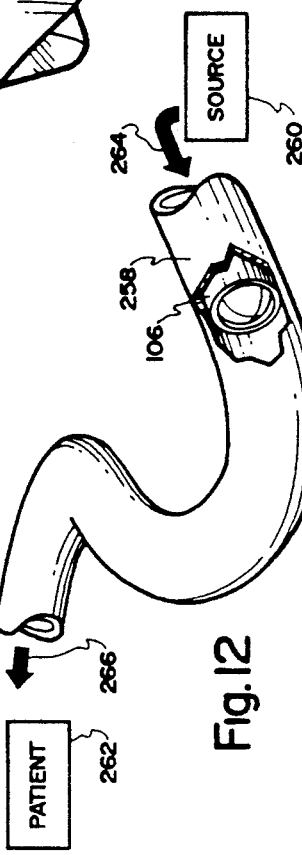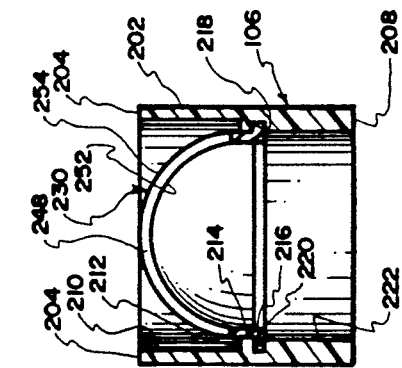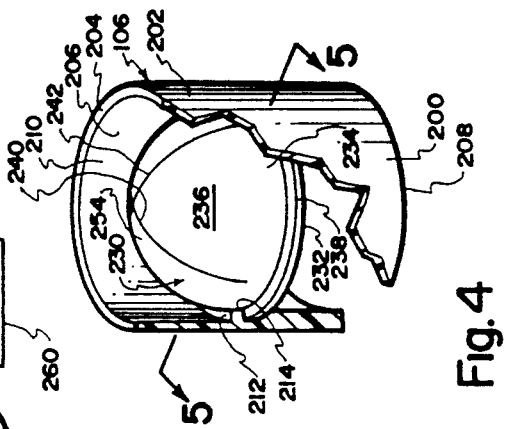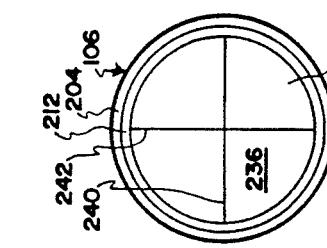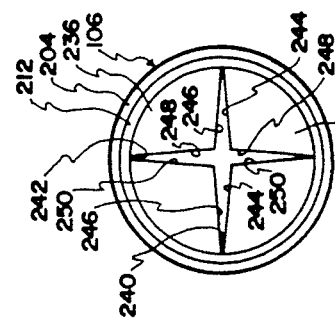

MEDICAL LAVAGE APPARATUS AND METHODS

CONTINUITY

This application is a division of our co-pending U.S. patent application Ser. No. 07/923,706, filed Jul. 31, 1992, now U.S. Pat. No. 5,254,086.

FIELD OF INVENTION

This invention relates broadly to medical lavage apparatus including medical valves and particularly to medical lavage apparatus comprising at least one novel slit valve selectively accommodating one-way flow of lavage solution and/or other physiological liquids.

BACKGROUND AND RELATED ART

Lavage is defined as the washing out of hollow organs by copious injection and reinjection of liquid. Gastric lavages, for example, are used for a wide variety of medical situations including poisonings, upper GI bleeding, ulcers, etc. The normal current method of performing such a gastric lavage involves the insertion of a tube into a patients's stomach through his nose or mouth.

According to principles disclosed in U.S. Pat. Nos. 4,842,581, 4,872,866, and 5,049,135 one lavage apparatus for delivering lavage solution quickly and efficaciously to a patient comprises a rigid housing defining side-by-side parallel irrigation and aspiration cylinders in which plungers are inserted from first ends thereof. The irrigation and aspiration cylinders have respective irrigation and aspiration check-valves at second ends thereof and inlet and outlet check-valves at sides thereof. An anti-venturi septum extends to an intersecting line from the second ends of the cylinders. This septum comprises two tapered, semi-circular-in-cross-section, baffles which meet at a sharp V-shaped apex which also forms a U-shaped intersection line to provide a full opening between a separate common exchange tube and both cylinders. The separate common exchange tube, with the common nozzle is attached to the housing surrounding the second ends of the cylinders and said septum. The internal size of the nozzle is about the same size as the inlet and outlet openings at the sides of the cylinders.

Check-valves disclosed in the above-mentioned U.S. Patents comprise flat resilient membranes attached to an exterior transverse wall of a valve bore which flex to open when pressure is exerted into the bore of the check-valve and return to a flat, closed disposition against the transverse wall of the valve when pressure is exerted in an opposite direction against the resilient membrane. One of the problems related to the use of flat membrane check-valves, as noted in U.S. Pat. Nos. 4,842,581 and 4,872,866, is jamming such as is caused by incomplete valve passage of non-liquid or high viscosity matter which is a common by-product of lavage procedures. In an attempt to find a solution for the jamming problem, flow orifice reducing shelves are installed in the flow path of the lavage solution upstream from the valves in order to allow larger surface-area membrane valves to be used because larger surface area flat membrane check-valves are not as susceptible to jamming as smaller surface area flat membrane check-valves.

BRIEF SUMMARY AND OBJECTS OF THE INVENTION

One of the primary applications for this invention is in lavage devices similar to the apparatus disclosed in U.S. Pat. Nos. 4,842,581, 4,872,866, and 5,049,135. In brief summary, this novel invention alleviates known problems related to jamming in lavage delivery apparatus by liquids containing non-liquid and high viscosity matter trapped in flat membrane check-valves. While the instant invention comprises lavage apparatus and novel one-way valving structure therefor, the novel valving structure eliminates the need for special shelving and for larger-than-flow orifice flat membrane check-valves in lavage apparatus.

The present invention embraces a lavage delivery apparatus comprising a novel one-way slit valve wherein highest velocity liquid flow occurs generally across the valve. The lavage slit valve, in its preferred configuration, comprises a hollow dome-shaped flexible membrane comprising at least one but preferably two medially intersecting slits. The slit lips comprise smooth opposing parallel walls such that when a positive pressure differential is applied toward the convex side of the dome, the lips are pushed together to form a tight seal thereby preventing reversal of flow. Conversely, when a positive pressure differential is applied toward the concave side of the dome, the slit lips separate medially to accommodate one-way controlled flow.

Accordingly, it is a primary object to provide a medical lavage apparatus comprising a novel one-way slit valve which selectively passes a physiological liquid.

It is another primary object to provide a medical lavage apparatus comprising a novel dome-shaped, one-way slit valve which functions as a check-valve in an aspirating line.

It is another primary object to provide a medical lavage apparatus comprising a novel dome-shaped, one-way slit valve which functions as a check-valve in an inspirating line.

It is a principal object to provide an improved medical lavage syringe apparatus comprising guides for plungers reciprocated therein such that handles attached to such plungers for manual reciprocation thereof are held in a desired predetermined alignment at all times.

It is another principal object to provide a medical lavage apparatus comprising a stop within a cylinder within which a plunger reciprocates to prevent the plunger from being totally withdrawn from the cylinder during operation.

It is a fundamental object to provide a medical lavage apparatus comprising a slit valve defining a pathway for selective one-way liquid flow and check valve features preventing fluid flow in the opposite direction.

These and other objects and features of the present invention will be apparent from the detailed description taken with reference to accompanying drawings.

BRIEF DESCRIPTION OF THE DRAWINGS

FIG. 1 is a perspective of the lavage apparatus of an embodiment of this invention with some parts illustrated diagrammatically;

FIG. 2 is an exploded perspective of the lavage apparatus of FIG. 1;

FIG. 3 is a perspective of a flat membrane check-valve;

FIG. 4 is a perspective of a dome-shaped, slit check-valve with parts broken away for clarity;

FIG. 5 is a cross-section taken along lines 5—5 of FIG. 4;

FIG. 6 is a top view of the dome-shaped, slit check-valve of FIG. 4 in a partially open condition;

FIG. 7 is a top view of the dome-shaped, slit check-valve of FIG. 4 in a closed condition;

FIG. 8 is a perspective of a plunger guide-stop;

FIG. 9 is a cross-section taken along lines 9—9 of FIG. 8;

FIG. 10 is a fragmentary perspective, with parts broken away for clarity of a port associated with a cylinder in the lavage apparatus of FIG. 1, with the dome-shaped, slit valve mounted in the port in a direction causing the cylinder to be part of an inspirating pump;

FIG. 11 is a perspective of a housing comprising parts associated with a port attached to the cylinder shown in FIG. 10, with parts broken away for clarity, wherein the dome-shaped, slit valve is mounted in the port in a direction which causes the cylinder to be part of an inspirating pump;

FIG. 12 is a fragmentary perspective of a line from a liquid source to a patient with some parts shown diagrammatically, the line having a dome-shaped, slit check-valve disposed therein;

FIG. 13 is a cross-section taken along lines 13—13 of FIG. 2 of a portion of the distal end of a plunger and an associated seal used in a cylinder of the lavage apparatus of FIG. 1; and FIG. 14 is a cross-section of a seal taken along lines 14—14 of FIG. 2, the seal shown attached to a portion of a plunger.

DETAILED DESCRIPTION OF THE ILLUSTRATED EMBODIMENTS

In this description, the term proximal is used to indicate the segment of the device normally closest to an operator or user of the device. The term distal refers to the other end. Reference is now made to the embodiments illustrated in FIGS. 1-14 wherein like numerals are used to designate like parts throughout.

A lavage apparatus 10 is shown in FIG. 1 for use with a supply container 12, supply tube 14, a waste container 16 and a waste tube 18. As better seen in FIG. 2, lavage apparatus 10 comprises a rigid housing 20, a common exchange tube 22 permanently affixed to housing 20 when assembled, an irrigation plunger 24, an aspiration plunger 26, and a system of seals and valves associated therewith.

Rigid housing 20 is preferably molded as one piece of medical grade, translucent styrene acrylonitrile plastic. Rigid housing 20 has an irrigation cylinder 28 defining an irrigation-cylinder bore 30, an aspiration cylinder 32, defining an aspiration cylinder bore 34, first and second supporting flanges 36 and 38 holding together first ends of irrigation and aspiration cylinders 28 and 32, a third flange 40 holding together second ends of irrigation and aspiration cylinders 28 and 32, an inlet port 42 located near the second end of irrigation cylinder 28, an outlet port 44 located near the second end of aspiration cylinder 32, an irrigation check-valve cylinder 46 located at the end of irrigation cylinder 28 and an aspiration check-valve cylinder 48 located at the second end of aspiration cylinder 32 and an anti-venturi septum 50 joining the second ends of irrigation and aspiration check-valve cylinders 46 and 48. As can be seen in FIGS. 1 and 2, first, second, and third flanges 36, 38, and 40 hold irrigation cylinder 28 and aspiration cylinder 32 in a side-by-side, parallel, relationship. The bores 30 and 34 of the respective irrigation and aspiration cylinders 28 and 32 are the same size, each preferably providing approximately 160 cc's in actual stroke volume, The inlet and outlet ports 42 and 44 are close to second ends 52 of irrigation and aspiration cylinders 28 and 32, in the form of small, equal sized valve cylinders extending perpendicular to axes of irrigation and aspiration cylinders 28 and 32. Such small sized valve cylinders increase the turbulence of fluid flow allowing for increased mixing and dissolution of aspirated contents, thereby, reducing incompetence in valves which may be subject to jamming and clogging.

As seen in FIG. 2, equal sized irrigation and aspiration check-valve cylinders 46 and 48 are connected to their respective irrigation and aspiration cylinders 28 and 32 by tapered bonnets 54 and 56, respectively, so as to be close to, and parallel with, one another. In this respect, the circumference of check-valve cylinders 46 and 48 is preferably about half that of irrigation and aspiration cylinders 28 and 32 and their axes are offset from those of irrigation and aspiration cylinders 28 and 32 so that irrigation and aspiration check-valve cylinders 46 and 48 are close to one another with their bores aligned with irrigation and aspiration cylinder bores 30 and 34.

Septum 50 has an irrigation baffle 58 and an aspiration baffle 60 each of which is semi-circular in cross-sectional shape. These baffles intersect at an outer tip 62 which forms a U-shaped line. In this regard, septum baffles 58 and 60 are only positioned on the inside sides of check-valve cylinders 46 and 48 so as to guide fluid from and to check-valve cylinders 46 and 48. A fourth flange 64 interconnects the outer ends of check-valve cylinders 46 and 48 and forms an oval with these outer ends.

Plungers 24 and 26 are molded to be identical, each having shafts comprised of crossed slats 66 and 68 supported by centrally disposed intermediate ribs 70 and end ribs 70'. Also molded integral therewith are finger-engaging handles 72 and seal mounting ribs 74. Each seal-mounting rib 74 is separated from the nearest supporting rib 70' by a space 76 into which internally directed rib 78 of seal 80 is inserted (see FIG. 13). There are three cylinder bore contacting rings 83a, 83b, and 83c on the outer surface of seal 80.

It should be noted from FIGS. 1 and 2 that finger-engaging handles 72 of plungers 24 and 26 are respectively turned so that they provide mirror images, one of the other. In this respect, finger-engaging handles 72 are not symmetrical, being flat at first sides 86 thereof and rounded at second sides 88 thereof. The reason for this is so that the first sides 86 can be as close together between two adjacent fingers as possible where it is desirable to operate the syringes simultaneously. Thus, although the plungers are not connected, these finger engaging portions are designed to allow easy use of one of the plungers individually or both together, as is desired. This allows one to "prime the pump", so to speak, with the irrigation half of the system prior to beginning a lavage procedure.

As seen in FIG. 2, each cylinder 28 and 32 comprises two access holes 86', 86", 88', and 88" respectively. A plunger guide-stop 90' is inserted into each access hole 86', 86", 88', 88" after each plunger 24 and 26 has been inserted into each cylinder 28 and 32 during final assembly. Referring to FIGS. 8 and 9 each plunger guide-stop 90' comprises a cap 90" having an inferior side 91' which has a curvature which corresponds to the exterior curvature of cylinders 28 and 32. From the inferior side 91' of cap 90" two legs 93' and 93" distend to form a U-shaped guide slot 95' therebetween.

Referring again to FIG. 2, portions of each intermediate rib 70 are removed providing a free strip 95" along slat 68 about which legs 93' and 93" can pass unencumbered as each plunger 24 and 26 is reciprocated within each respective cylinder 28 and 32. Note that such portions are not removed from rib 70'. Thus, when guide-stops 90' are fully inserted into access holes 86' and 88', each distal rib 70' engages an associated guide-stop 90' as each plunger 24 and 26 is withdrawn proximally to cause plungers 24 and 26 to be permanently retained in cylinders 28 and 32. Further, each slat 68 is disposed between at least one pair of legs 93' such that rotational travel of each plunger 24 and 26 is limited, thereby keeping handles 72 relatively disposed as seen in FIG. 1.

As part of the assembly of lavage apparatus 10, seals 80 are attached to each plunger 24 and 26 which is inserted into each cylinder 28 and 32 and handles 72 are oriented as seen in FIG. 2. When handles 72 are so oriented, slats 68 align with holes 86', 86", 88', and 88" in each respective cylinder 28 and 32. Legs 93' and 93" of one guide-stop 90' are inserted into each hole 86', 86", 88', and 88" such that each U-shaped 95' guide slot engages slat 68. Each guide-stop 90' is permanently affixed to each cylinder 28 and 32 by sonic welding or by adhesive techniques well known in the art. Each guide-stop 90' is preferably made from the same material as used for cylinder's 28 and 32 and formed by injection molding.

The common exchange tube 22 is oblong, or oval, in cross section as can be seen in FIGS. 1 and 2 to thereby form an oblong chamber in which fluid flows to and from irrigation and aspiration cylinders 28 and 32. The common exchange tube 22 includes an apron portion 90, a manifold portion 92, a common nozzle portion 94, and an attachment ridge 96. Attachment ridge 96 is of a size to sealingly fit about the side-by-side irrigation and aspiration check-valve cylinders 46 and 48 and the fourth flange 64 which joins them. In use, these members are preferably joined together by sonic welding or by an adhesive. The apron portion 90 makes the entire apparatus more streamlined in appearance and for handling, however, it is not necessary for operation of the lavage apparatus.

Manifold portion 92 encloses and seals with outer ends 98 and 100 of irrigation and aspiration check-valve cylinders 46 and 8 as well as septum 50 so that all material flowing to and from outer ends 98 and 100 are guided by septum 50 and manifold portion 92. Similarly, all fluids flowing to and from manifold portion 92 flow through common nozzle 94. It should be noted that septum 50 is so arranged and designed that fluid streams flowing from irrigation check-valve cylinder 46 is directed into nozzle 94 and fluid flowing from nozzle 94 is directed to aspiration check-valve cylinder 48 without restriction and without causing undue turbulence. In this manner, such fluid streams are not caused to cross mix. The U-shaped outer tip line 62 particularly aids in avoiding undue cross mixing by not causing a venturi restriction to create a negative pressure in manifold portion 92 which improperly opens a check-valve. Sidewalls of septum 50 press against interior surfaces of the manifold to create a seal therebetween.

To assure a secure attachment to a patient connection tube (not shown) nozzle 94 comprises a tube retaining apparatus 94' seen in FIGS. 1, 2, and 14. Referring to 14, tube retaining apparatus 94' is therein seen in cross section. Tube retaining apparatus 94' comprises two identical molded, sections 97 and 97' which oppose each other about nozzle 94. As both molded sections 97 and 97' are identical, only one section 97 will described in detail.

Tube retaining apparatus 94' is attached to nozzle 94 through an offsetting ring 97" which encircles nozzle 94 and provides attachment for both sections 97 and 97'. Distending proximally from offsetting ring 97" is an ear-shaped part 99 which is shaped for engagement by an operator's thumb and fingers. Extending distally from offsetting ring 97" is a tube engaging part 99' which is shaped to engage the patient tube when disposed upon nozzle 94. A strengthening member 100' is disposed between parts 99 and 99' to transfer at least a portion of the forces exerted upon part 99 to part 99'. So disposed, when parts 99 of both sections 97 and 97' are forced inward, by squeezing such as by a thumb and forefinger, parts 99' are moved away from nozzle 94 to permit the patient connection tube to be facilely connected thereto. After insertion of the patient connection tube, the compressive force against sections 97 and 97' is released and each part 99' compressively engages the patient connection tube. A secure engagement is further secured by a plurality of grooves 100" molded into each part 99' to act as teeth which bite into the patient connection tube to better secure the patient connection tube after release of parts 99'.

With regard to the check-valves, two different types of check-valves are seen in the embodiment of FIG. 2. A first check-valve 102, valve 101, comprising a flat, resilient membrane 104 is disposed in inlet port 42 of irrigation cylinders 28. A second, like check-valve 102, valve 101' is disposed in irrigation check-valve cylinder 46. Each check-valve 102 is oriented with each cylinder 28 and 46 in a direction permissive to fluid flow toward nozzle 94.

As seen in FIG. 3, each check-valve 102 has a cylindrical outer wall 102" with a planar cylindrical edge 103 and cross wall struts 104' carrying resilient membrane 104. Between cross wall struts 104' a plurality of membrane supporting tines 104" project radially inward from outer wall 102". In combination, planar cylindrical edge 103, cross wall struts 104' and tines 104" define a membrane supporting planar surface 103'.

Referring again to FIG. 2, as an example of check-valve 102 operation, resilient membrane 104 on valve 101' flexes open when pressure is exerted from the irrigation cylinder bore 30 toward nozzle 94 but closes when pressure is exerted in the opposite direction. It should be noted that flow through an open check-valve 102 courses radially outward across surface 103' and around a peripheral edge 105 of membrane 104. Thus flow about membrane 104 is a relatively thin stream, cylindrically disposed about the outer edge 105 of membrane 104, best seen in FIG. 3. Any material resident upon surface 103' when membrane is forced thereagainst to close check-valve 102 can cause check-valve 102 to be incompetent. Such problems are not common for irrigation solutions, but when physiological debris is recovered from a patient during a lavage procedure, solid or highly viscous matter is commonly carried in aspirated solutions. For this reason, flat membrane check-valves are not as effective in aspirating pathways as in inspirating pathways of lavage apparatus.

For this reason in the embodiment seen in FIG. 2, a first dome-shaped, slit check-valve 106, valve 106" is used in aspiration check-valve cylinder 48 to restrictively control flow only into cylinder 32. Dome-shaped, slit check-valve 106 comprises novel non-jamming features more particularly qualified for use in check-valve applications involving valving solutions comprising physiological debris. A detailed description of dome-shaped, slit valve 106 is provided hereafter. A second dome-shaped, slit check-valve 106, valve 106' is disposed in outlet port 44 to serve as a physiological debris containing solution valve in the same manner and direction as valve 106".

As mentioned earlier, valve 101' is disposed in irrigation check-valve cylinder 46 and allows fluid to flow into irrigation cylinder 28, but does not allow flow from irrigation cylinder 28. Outlet valve 106" allows fluid flow from aspiration cylinder 32, however, it does not allow flow into cylinder 32. Funnel-like inlet and outlet adapters 116 and 118 are respectively attached to inlet port 42 and outlet port 44.

Regarding inlet and outlet ports 42 and 44, each port 42 and 44 preferably comprises a diametral opening substantially the same size as ports irrigation check-valve cylinder 46 and aspiration check-valve cylinder 48 such that valves may be used interchangeably in ports 42 and 44 and check-valve cylinders 46 and 48, as appropriate. Ports 42 and 44 open unobstructedly into cylinder bores 30 and 34, respectively. The approximate matching of the sizes of ports 42 and 44 and check-valve cylinders 46 and 48 balances pressures within the system so as to avoid improper opening check-valves during operation and thereby avoid cross mixing of contaminated and pure fluids.

Referring once more to FIG. 13, the distance between rings 83a and 83c is sufficient to cover each associated port 42 and 44 when each respective plunger 24 and 26 is fully seated in the respective cylinder bore 30 and 34, allowing ports 42 and 44 to be fully sealed by seal 80. Through the use of dome-shaped, slit check-valves 106, a previously taken precaution of shelving in each port opening between a port 42 or 44 and a respective cylinder bore 30 or 34 in embodiments of similar lavage apparatus is not required.

In manufacture of the lavage apparatus of this invention, rigid housing 20, two plungers 24 and 26, the common exchange tube 22 (assembled to be a part of the housing), and the various cylinders of the two check-valves 102 and 106, and inlet and outlet adapters 116 and 118 are molded of hard resinous plastic. In this respect, all of the check-valves are of the same size to eliminate undue proliferation of molds for these elements. All of the rigid components of this invention can be made of a rigid hard resinous plastic such as styrene acrylonitrile.

Plunger seal 80 and the various check-valve membranes are molded, or purchased off-the-shelf of pliant synthetic resinous material. The dome-shaped, slit membrane material and method of manufacture is described in detail hereafter. The plunger seals 80 are attached to plungers 24 and 26 and as seen in FIG. 3, membranes 104 are attached by outwardly distending portions 102' of knobs 105' medially disposed on check-valve 102 cross wall struts 104'. Exteriors of cylinders of check-valves 102 and check-valves 106 are preferably attached by sonic welding into rigid housing 20 in their respective positions as is depicted in FIG. 2. After attachment of check-valves 102 and 106, as appropriate, attachment ridge 96 of common exchange tube is sealingly adhered to irrigation and aspiration check-valve cylinders 46 and 48 and flange 64 which adjoins these two ridges, also preferably by sonic welding. As seen in FIG. 1, the various valves cannot be easily serviced, but that is not necessary since the lavage apparatus is designed to be a single use disposable product.

To utilize lavage apparatus 10, one places a saline liquid in supply container 12 which is joined via a supply tube 14 and inlet adapter 116 to inlet port 42. See FIG. 1. The waste container 16 is similarly attached via tube 18 and outlet adapter 118 to outlet port 44. The saline solution is to be instilled into a body cavity, left for a short length of time and then sucked out. A tube (not shown) is attached to nozzle 94 of the common exchange tube 22 and is inserted through an opening in the human body of a patient 119 in the direction of arrow 119' into an organ to be lavaged. Where fluid from more than one irrigation cylinder 28 is to be inserted into the organ before any is aspirated, aspiration plunger 26 is driven completely into aspiration cylinder 32 as is depicted in FIG. 1. In this position, aspiration plunger seal 80 completely seals outlet port 44. Thus, while the aspiration plunger 26 is left in this position, no fluid can flow through outlet port 44. With aspiration plunger 26 so situated, the irrigation plunger 24 is pulled outwardly to cause a vacuum in the irrigation cylinder 28. This vacuum respectfully opens membrane 104 of inlet check-valve 101 and closes membrane 104 of check-valve 101'. Thus fluid is drawn from supply container 12 into irrigation cylinder 28. Thereafter, irrigation plunger 24 is driven into irrigation cylinder 28 which closes inlet check-valve 101, opens irrigation check-valve 101', and drives fluid out of irrigation cylinder 28 into manifold portion 92 of common exchange tube 22 and out nozzle 94 of common exchange tube 22. In this respect, irrigation baffle 58 of septum 50 guides the outwardly flowing fluid to ensure that it enters nozzle 94 rather than being driven through aspiration check-valve cylinder 48 to open aspiration check-valve 106" and thereby drive plunger 26 from its blocking position. The irrigator plunger 24 is moved in and out, functioning as a pump, until the body cavity is filled with the right amount of fluid.

After the irrigation fluid has been left in the body organ for a period of time, irrigation plunger 24 is driven fully into irrigation cylinder 28 so seal 80 covers port 42 thereby not allowing flow of fluid through port 42. Once irrigation plunger 24 is so seated, aspiration plunger 26 is pulled and pushed in, thereby drawing contaminated fluid from the body organ through nozzle 94, and aspiration check-valve cylinder 48, into aspiration cylinder 32 during the pull and driving contaminated waste fluid out of port 44 and into waste container 16 during the push.

Ordinarily, most body organs requiring lavage will be of such size as to hold multiple loads of irrigation cylinder 28, with the skill of an operator protecting against over distension of a cavity. Once the appropriate amount of irrigant is instilled, irrigation and aspiration plungers 24 and 26 are gripped together and moved in and out simultaneously thereby maintaining a constant steady-state volume of fluid flow into and out of the organ. On the out strokes irrigation cylinder 28 is loaded with fresh fluid from supply container 12 and aspiration cylinder 32 is loaded with contaminated, physiological debris containing waste solution from the organ. On in strokes, the fresh fluid in irrigation cylinder 28 is forced into the organ and contaminated waste fluid in aspiration cylinder 32 is forced toward and into waste container 16. During these strokes, since ports 42 and 44 have the same cross-section size as the internal bore of nozzle 94, the pressures applied at each of these by the equal size plunger 24 and 26 are approximately equal, there being only a small drop across each of the various valves to cause them to act as check-valves in the appropriate directions. Similarly, the shape of the U-shaped outer tip line 62 of septum 50 does not cause undue venturi or eddy effects which create undue changes in pressure at nozzle 94 to improperly open irrigation and aspiration check-valves 101' and 106" to cause mixing.

A unique feature of the design of this lavage apparatus is that it can be used to clear itself of debris. In this regard, the most likely occlusion will occur on the aspiration side of the device because it is the part which is exposed to particulate matter. If a clog should develop, one can clear it by pulling back on aspiration plunger 26 until outlet port 44 is open, crimping of the tube attached to nozzle 94, and pumping irrigation plunger 24 in and out to force fresh fluid through aspiration check-valve 106" and outlet check-valve 106'. The tube attached to nozzle 94 can be cleared by pushing aspiration plunger 26 fully forward to seat and close port 44, followed by forcefully operating irrigation plunger 24.

A significant improvement in lavage apparatus operation as a result of a reduction in need to clear debris from valves and improved operational valve competency while operating an lavage produced physiologic debris containing solution environment is accrued through use of check-valves which open a medially disposed pathway to fluid flow rather than a pathway about a planar edge as is true of flat membrane valve 102. As described earlier, such check-valves 106 are used in the embodiment seen in FIG. 2 as valves 106' and 106". Magnified views of check-valve 106 are seen in FIGS. 4–7.

As seen in FIG. 4, valve 106 comprises a slit membrane surrounding cylindrical housing 200. Housing 200 comprises an outer cylindrical surface 202, a top circular edge 204, an inner cylindrical surface 206, and a bottom circular edge 208. While surface 202 is smooth and of uniform diameter for being inserted and affixed to an inward disposed surface such as to a port 44, inner surface 206 comprises a series of steps and grooves such that circular edge 204 is thinner in radial width than edge 208. As seen in FIG. 4, inner surface 206 comprises a surface of revolution which comprises a side wall 210 which departs from edge 204 travelling parallel to outer wall 202 to a radially inwardly projecting ledge 212 which is truncated by a second parallel surface 214 which is parallel to outer wall 202. More proximal to edge 208, parallel surface 214 intersects with a surface 216 radially distending outwardly therefrom. Surface 216 intersects with a third parallel surface 218 which is parallel to outer wall 202. Surface 218 is truncated by a surface 220 which radiates inwardly from surface 218 to a fourth parallel surface 222 which is parallel to outer wall 202. So disposed, surfaces 216, 218, and 220 form a retaining groove for a dome shaped, slit valve membrane 230.

As best seen in FIG. 4, dome shaped, slit valve membrane 230 comprises a base 232, a hollow cylindrical side wall 234, and a hollow dome 236. As seen in FIGS. 4 and 5, base 232 comprises an anchoring ring 238 which extends radially outward from side wall 234, is formed and shaped to fit tightly within the groove formed by surfaces 216, 218, and 220 and is hermetically secured in housing 200 by insertion into the groove formed by surfaces 216, 218, and 220.

From base 232, membrane 230 is seen in FIG. 4 to extend upward to form cylindrical side wall 234 to which is attached enclosing dome 236. Dome 236 comprises at least two intersecting slits 240 and 242, which preferably intersect medially at the top of dome 236 at right angles. Each slit 240 and 242 comprises a pair of smooth, planar, opposing lips 244, 246, 248, and 250, respectively, best seen in FIG. 6. Referring briefly to FIG. 5, dome 236 comprises a hollow, circular concave inner surface 252 and an outer convex surface 254 which is circularly parallel to surface 252. As best seen in FIG. 7, when a positive pressure is exerted upon surface 254, opposed lips 244, 246, 248, and 250 are forced closed by a radial force vector of the surface imposed pressure while the dome shape of membrane 230 resists eversion, even to pressures which are large compared pressures exerted during a lavage procedure.

As seen in FIG. 6, when a positive pressure is applied to inner surface 252, lips 244, 246, 248 and 250 are forced apart, creating a centrally disposed orifice which is permissive to flow therethrough. As is well known in the art of fluid flow, fluid flow velocity is higher, the farther away from a wall fluid is flowing in a tube. As such, it has been shown that the best valve for transport of physiologic debris carrying solutions is one which opens widely and centrally to permit solution to medially flow across the valve with highest possible velocity. Also, as membrane 230 presents a slick, surface with nearly unattachable edges of lips 244, 246, 248, and 250, jamming of valve 106 due to solids or high viscosity liquids in contact therewith is rare, making use of membrane 230 ideal for valving of physiological debris carrying solutions.

Housing 200 may be made by injection molding and may be made from rigid synthetic resinous material such as the material from which housing 20 is made. Membrane 230 may be made from a flexible, resilient synthetic resinous material such as KRATON, a product of GLS Plastics, 740 B, Industrial Park, Carey, Ill., 60013. Membrane 230 is preferably made by injection molding with each slit 240 and 242 being individually cut therein by using a razor sharp blade which cuts one slit of the membrane at a time while residing upon a membrane 230 form-fitting tool which comprises slits matching the width and direction of cut of the sharp blade.

It can be appreciated by those skilled in the art that the lavage apparatus described herein is relatively easy to manufacture and use but yet allows non-messy lavaging of organs. Medical personnel can perform lavage procedures without the lavage liquid escaping outside the system and therefore not contaminating lavage personnel, a patient, nor surrounding areas and not otherwise causing an unsanitary or disagreeable problem.

The designs of smaller, offset, irrigation and aspiration check-valve cylinders 46 and 48, pointed plunger seals 80 and the common exchange tube 22 which is welded directly to housing 20 creates a minimum of "dead space" between irrigation and aspiration check-valve cylinders 46 and 48 and nozzle 94 which improves pumping efficiency.

The design of septum 50 prevents undue eddy and venturi effects.

In another embodiment of the invention, a valve 106 is used to replace valve 102 in port 42 as seen in FIG. 11. As valve 106 comprises a housing 200 which is substantially the same size as outer wall 102" replacement is a direct one-to-one substitution.

In yet another embodiment of the invention a valve 106, is used instead of valve 102 in irrigation check-valve cylinders 46 as seen in FIG. 10. As is the case in the embodiment of FIG. 11, valve 106 is a direct replacement for valve 102 in this embodiment as well.

A different application for valve 106 is seen in an embodiment shown FIG. 12 wherein a valve 106 is used in a medical line 258 from a source 260 to a patient 262. Connections and fluid flow from source 260 to line 258 and from line 258 to patient 262 are symbolized by arrows 264 and 266, respectively. As seen in FIG. 12, valve 106 is disposed in line 258 in a direction permissive to flow from source 260 to patient 262. So disposed, valve 106 blocks block bleed back when line 258 transmits a higher than source pressure from a vessel or cavity in patient 262.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method for removing aspired physiological liquids through check-valves which remain competent during a lavage procedure comprising the steps of:
    connecting a double cylinder medical lavage apparatus to a patient body cavity communicating tube;
    proximally reciprocating a pair of plungers of the double cylinder medical lavage apparatus to draw wash liquid into one cylinder while drawing physiological debris through the communicating tube toward and into the other cylinder;
    passing liquid through a first centrally disposed flow pathway formed by a first dome-shaped, slit stop valve for liquid flowing from said communicating tube to said other cylinder;
    distally reciprocating said pair of plungers to flush wash liquid through the communicating tube toward and into the patient body cavity while competently closing the first centrally disposed flow path of said first stop valve and pumping the physiological debris to a waste container out of the other cylinder;
    passing the physiological debris through a second centrally disposed flow pathway formed by a second dome-shaped, slit stop valve for liquid flowing from the other cylinder to a waste container, said second stop valve competently closing the second centrally disposed flow pathway during the proximally reciprocating step.

2. A method of introducing lavage into a patient comprising the steps of:
    connecting a source of medical liquid to a syringe mechanism to accommodate selective influent liquid flow;
    limiting liquid flow between the source and the syringe mechanism to one-way flow by positioning a one-way slit valve between the source and the syringe mechanism;
    causing influent liquid flow to the syringe mechanism by creating a predetermined pressure differential across the slit valve sufficient to flex a slit thereof distally;
    preventing reversal of flow between the syringe mechanism and the source by creating a predetermined pressure differential across the slit valve sufficient to close the slit thereof proximally.

3. A method of aspirating liquid and physiological debris from a body cavity of a patient comprising the steps of:
    placing a liquid and physiological debris influent port of an aspirating cylinder comprising an interior in selective flow communications with the body cavity;
    placing a liquid and physiological debris effluent port of the aspirating cylinder in flow communication with a discard site;
    manually reciprocating a plunger in the aspirating cylinder to create pressure to thereby displace liquid and physiological debris along a flow path comprising the influent port, the interior of the aspirating cylinder and the effluent port, said pressure causing normally closed contiguous directly abutting edges of at least one slit in an arched wall of a diaphragm disposed int he flow path to separate thereby creating an opening through which said liquid and physiological debris facilely passes.

4. A method of irrigating and aspirating a body cavity of a patient comprising the steps of:
    providing a liquid irrigation cylinder having an interior and a plunger, the irrigation cylinder having a liquid influent port and a liquid effluent port;
    providing a liquid and physiological debris aspiration cylinder having an interior and a plunger, the aspiration cylinder having a liquid and debris influent port and a liquid and debris effluent port;
    displacing irrigating liquid to the body cavity via the liquid influent port, the interior of the liquid irrigation cylinder and the liquid effluent port responsive to manual reciprocation of the liquid irrigation plunger;
    displacing liquid and physiological debris from the body cavity along a flow path comprising the liquid and debris influent port, the interior of the aspiration cylinder, and the liquid and debris effluent port responsive to the manual reciprocation of the aspiration plunger, pressure due to said reciprocation accommodating displacement of the liquid and debris across at least one dome-shaped slit valve having at least one slit disposed in the flow path by spreading normally contiguously and abuttingly closed lip edges at the slit into spaced relation while retaining the edges in generally opposed alignment to create a flow opening at the slit.

5. A lavage method comprising the steps of:
    supplying medical irrigating liquid from a source;
    displacing medical irrigating liquid from the source selectively into a body cavity of a medical patient via an irrigating syringe;
    aspirating liquid and physiological debris from said body cavity using an aspirating syringe including passing the liquid and physiological debris across at least one rounded normally closed one-way slit valve diaphragm by flexing the diaphragm along at least one curved slit comprising normally closed opposed contiguous slit edges to spread the slit edges apart thereby defining an opening between the edges to accommodate facile flow of liquid and physiological debris through the opening.

* * * * *